(12) United States Patent  
Smallwood

(10) Patent No.: US 9,377,385 B2  
(45) Date of Patent: Jun. 28, 2016

(54) ROTATING DOVETAIL CONNECTION FOR MATERIALS TESTING

(71) Applicant: ILLINOIS TOOL WORKS INC., Glenview, IL (US)

(72) Inventor: James Brittain Smallwood, Milton, MA (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 14/854,246

(22) Filed: Sep. 15, 2015

(65) Prior Publication Data

US 2016/0069784 A1   Mar. 10, 2016

Related U.S. Application Data

(63) Continuation of application No. 12/322,386, filed on Feb. 2, 2009, now abandoned.

(60) Provisional application No. 61/069,815, filed on Mar. 18, 2008.

(51) Int. Cl.  
*G01N 3/04* (2006.01)

(52) U.S. Cl.  
CPC .......... *G01N 3/04* (2013.01); *G01N 2203/0016* (2013.01); *G01N 2203/0017* (2013.01); *G01N 2203/0268* (2013.01); *G01N 2203/04* (2013.01); *G01N 2203/0405* (2013.01); *G01N 2203/0423* (2013.01)

(58) Field of Classification Search  
CPC ............ G01N 3/04; G01N 2203/0017; G01N 2203/04; G01N 2203/0405

USPC .............................. 73/856–860; 279/121–123  
See application file for complete search history.

(56) References Cited

U.S. PATENT DOCUMENTS

| | | | |
|---|---|---|---|
| 295,628 A | 3/1884 | Gilmore | |
| 1,274,685 A | 8/1918 | Cline | |
| 2,523,374 A | 9/1950 | Jensen | |
| 2,993,701 A | 7/1961 | Arnold | |
| 3,170,322 A | 2/1965 | Cavanaugh | |
| 3,224,259 A * | 12/1965 | De Nicola | G01N 3/04 279/66 |
| 3,248,121 A | 4/1966 | Volpe | |
| 3,403,549 A * | 10/1968 | Griffin | G01N 3/04 73/859 |
| 3,413,010 A | 11/1968 | Buck | |
| 3,494,627 A | 2/1970 | Pirman | |
| 3,583,717 A | 6/1971 | Hall et al. | |
| 3,679,221 A | 7/1972 | Behrens | |

(Continued)

FOREIGN PATENT DOCUMENTS

| | | |
|---|---|---|
| DE | 3926308 | 2/1991 |
| DE | 69628898 | 5/2004 |

(Continued)

*Primary Examiner* — Lisa Caputo  
*Assistant Examiner* — Jonathan Dunlap  
(74) *Attorney, Agent, or Firm* — McCarter & English, LLP

(57) ABSTRACT

A rotating dovetail connection is provided in order to attach jaw faces to grips in materials testing. The connection includes a machined tongue on the jaw face and a corresponding groove on the jaw face holder. A ball plunger within the holder serves to center the jaw face and to retain the jaw face in the holder. The jaw faces can be installed an removed without the use of tools or loose parts. The rotating dovetail facilitates a secure connection between the jaw face and the grip while allowing the jaw faces to rotate.

4 Claims, 7 Drawing Sheets

(56) References Cited

U.S. PATENT DOCUMENTS

| | | | |
|---|---|---|---|
| 3,833,232 A | 9/1974 | Behrens | |
| 4,353,561 A | 10/1982 | Peterson | |
| 4,730,498 A * | 3/1988 | Blanch | G01N 3/20 73/852 |
| 4,888,995 A * | 12/1989 | Curtis | G01N 3/04 73/859 |
| 4,909,085 A * | 3/1990 | Hardy | G01N 3/24 73/833 |
| RE33,409 E * | 10/1990 | Curtis | G01N 3/04 73/859 |
| 6,237,422 B1 | 5/2001 | Sykes | |
| 7,500,401 B2 | 3/2009 | Tsai | |
| 7,537,218 B2 * | 5/2009 | Wachtler | B23B 31/1602 279/112 |
| 7,540,201 B1 * | 6/2009 | Hemmerlin | G01N 3/04 73/856 |
| 7,793,553 B2 * | 9/2010 | Lindeman | G01N 3/04 73/760 |
| 7,827,868 B2 * | 11/2010 | Lindeman | G01N 3/04 73/760 |
| 8,281,666 B2 * | 10/2012 | Jevons | G01N 3/08 73/818 |
| 2002/0166387 A1 * | 11/2002 | Grote | G01N 3/04 73/857 |
| 2009/0139343 A1 * | 6/2009 | Lindeman | G01N 3/04 73/856 |

FOREIGN PATENT DOCUMENTS

| | | |
|---|---|---|
| EP | 0070480 | 9/1987 |
| JP | 59133818 | 8/1984 |
| JP | S62167433 | 7/1987 |
| JP | H0229820 | 7/1990 |
| JP | 2550804 Y2 | 10/1997 |

* cited by examiner

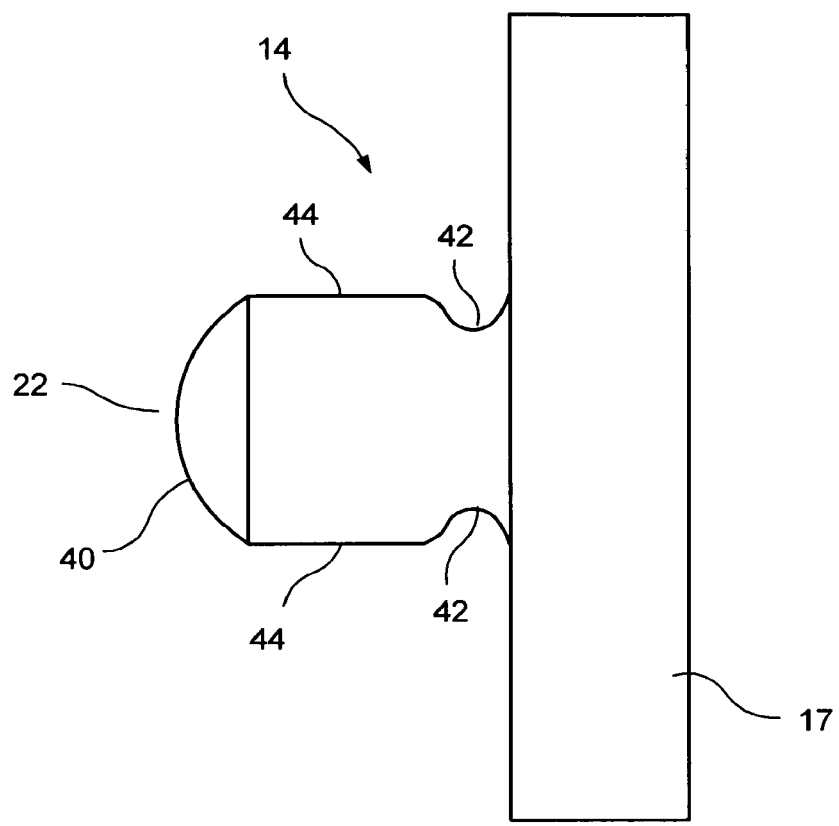
F I G. 10 ial testing equipment and accessories. More specifically, the
ROTATING DOVETAIL CONNECTION FOR MATERIALS TESTING This application is a continuation of U.S. patent application Ser. No. 12/322,386, filed on Feb. 2, 2009 which claims priority under 35 U.S.C. 119(e) from U.S. provisional patent application Ser. No. 61/069,815, filed on Mar. 18, 2008, the contents of which are hereby incorporated by reference.

BACKGROUND OF THE INVENTION

1. Field of the Invention

The present invention pertains to a device for use in material testing equipment and accessories. More specifically, the present invention pertains to a mechanism for the connection of removable jaw faces to material testing grips.

2. Description of the Prior Art

In the prior art, materials testing systems are used in a variety of industries and are generally used with some sort of accessory to provide specimen gripping or holding. Many of these tests require that the accessories have specific gripping surfaces or sizes. The size and type of gripping surface needed can vary greatly from test to test, making jaw face changes a frequent event in many labs. Therefore, removable jaw faces with various sizes and surfaces are a common commodity in the materials testing industry.

Many different embodiments of jaw face attachment have developed over the years by various manufacturers. These connection mechanisms include simple pin and aperture connections as well as rigid dovetail connections. Each mechanism has advantages and disadvantages.

Zwick has implemented the use of a rigid dovetail connection as shown in FIG. 1. This connection method allows for a repeatable location for the jaw face while allowing for ease of installation. Rotation of the jaw faces is not possible with this method rendering fixed the position of the jaw faces relative to the gripped specimen. Furthermore, a tool must be used to connect these jaw faces to their holders.

MTS has implemented an externally accessible pin and a corresponding aperture to connect the jaw faces to the grips as shown in FIG. 2. This allows for jaw face rotation but poses a potential safety issue because the protruding heads and rings of the pins also move in conjunction with the jaw faces. The pull rings used for removing the pins may also get entangled in the grips. External pins may also be ejected from the apertures if measures are not taken to retain them in the grips. It appears that this has been addressed with the addition of an O-ring to the end of the pin. Additionally, the pins are a loose part which may be easily lost.

Instron, the assignee of the present application, has implemented four jaw face to grip connection methods of interest. These method include set screw and groove; internal pin an aperture; internal pin and retaining wire; and hook and fixed pin. All of these methods allow the jaw faces to rotate. This rotation is needed to compensate for both inconsistencies in specimen thickness and elastic deformation of grip bodies during testing. The set screw and groove method as shown in FIG. 3 is a simple and inexpensive method that requires a tool for installation. The set screws provide the pivot point for jaw face rotation. Faces typically rotate slightly in all directions with this connection method.

The internal pin and aperture method as shown in FIG. 4 has been perhaps the most common jaw face connection method used to date and has been adopted by various competitors. While this is perhaps the least expensive and least complicated method, there are some drawbacks. For instance, installation often requires an experienced user or an additional person to hold and manipulate the various components. Additionally, the pins may not maintain their positional integrity during testing. A slight displacement may typically be remedied by the retraction of the holders into the grip body, but occasionally it results in the pin and jaw face falling partially or completely out of the holder. Another drawback is that the pins are small loose parts which can be easily dropped or lost.

The internal pin and retention wire method was developed by the present assignee for use on side-acting screw action grips and uses a semi-permanent pin installed in the back of a typical pin and aperture jaw face as shown in FIGS. 5A and 5B. This assembly can be snapped into the holder using one hand and without the use of any tools. To remove the jaw face, simply unscrew the holder until the retention wire opens up. The jaw face can now be easily removed. While this method allows for simple installation and predictable usage patterns, there are some drawbacks associated with it. Firstly, the retention wire and holder both require special detailed machine to get the correct feel and action. Secondly, the semi-permanent pin represents a small loose part that can get lost.

On higher capacity pneumatic side-action grips, the present assignee has implemented the use of a hook and fixed pin connection method as shown in FIG. 6. A fixed pin is pressed into the back of a specially machined jaw face and acts as an attachment point for a corresponding spring-loaded hook that resides inside of the grip. Attaching the face to the grip requires that the user insert a tool onto the grip to move the spring-loaded hook far enough to slide the face over it. When the hook retracts back into the body, the face is firmly held on the grip. This eliminates loose parts, but necessitates the use of a tool for installation and removal. This apparatus further requires unique detailed faces and holders.

OBJECTS AND SUMMARY OF THE INVENTION

It is therefore an object of the present invention to provide a connection apparatus for materials testing which is easy to operate, is robust, and provides repeatable jaw face positioning.

It is therefore a further object of the present invention to provide a secure rotating jaw face connection to be used in material testing accessories which substantially eliminates the complexity and difficulty involved in installing and removing jaw faces.

It is therefore a still further object of the present invention to reduce or eliminate the need for tools in the assembly and disassembly of the connection apparatus for materials testing, while maintaining secure operation of the apparatus.

These and other objects are attained by providing a rotating dovetail connection for use on materials testing accessories that use removable jaw faces. This rotating dovetail connection is related to the dovetail joinery connection that allows for a secure sliding connection in carpentry without the use of auxiliary parts. Adapting the tongue and groove of the joint into a rounded edge permits the connection to rotate while still being held securely together. This is particularly useful in jaw face attachment where slight rotation of the jaw faces is desired. The tongue also has a decent machine into the back side to permit a spring loaded ball to hold the jaw face securely and accurately in the holder. The degree of rotation is controlled by the placement of the groove in relation to the back of the jaw face. Another embodiment machines flats and a cross aperture on the jaw face for to allow use in grips that use the pin and aperture connection method.

BRIEF DESCRIPTION OF THE DRAWINGS

Further objects and advantages of the invention will become apparent from the following description and from the accompanying drawings and claims, wherein:

FIG. 10 is a plan view of the rotating dovetail gripping mechanism of an embodiment of the present invention.

DETAILED DESCRIPTION OF THE PREFERRED EMBODIMENT

Figure 1:
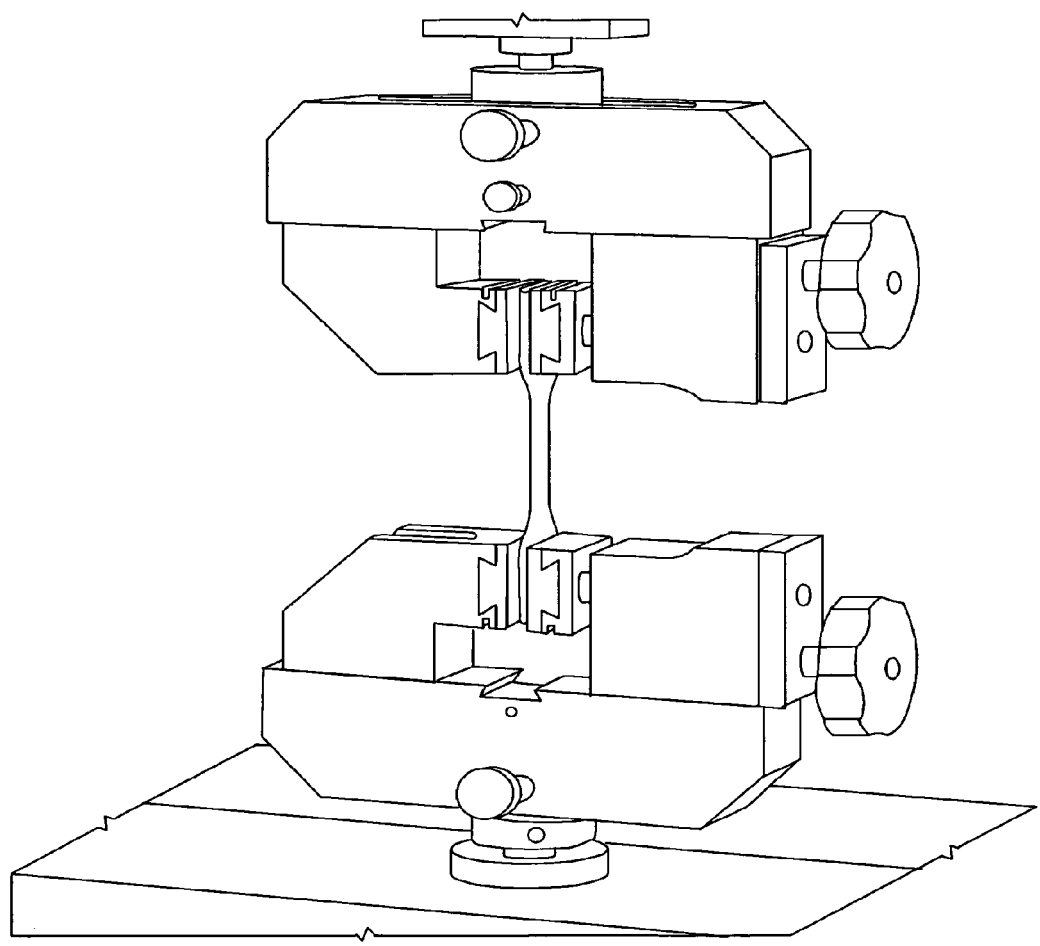
FIG. 1 illustrates typical prior art dovetail connection apparatus.
Figure 2:
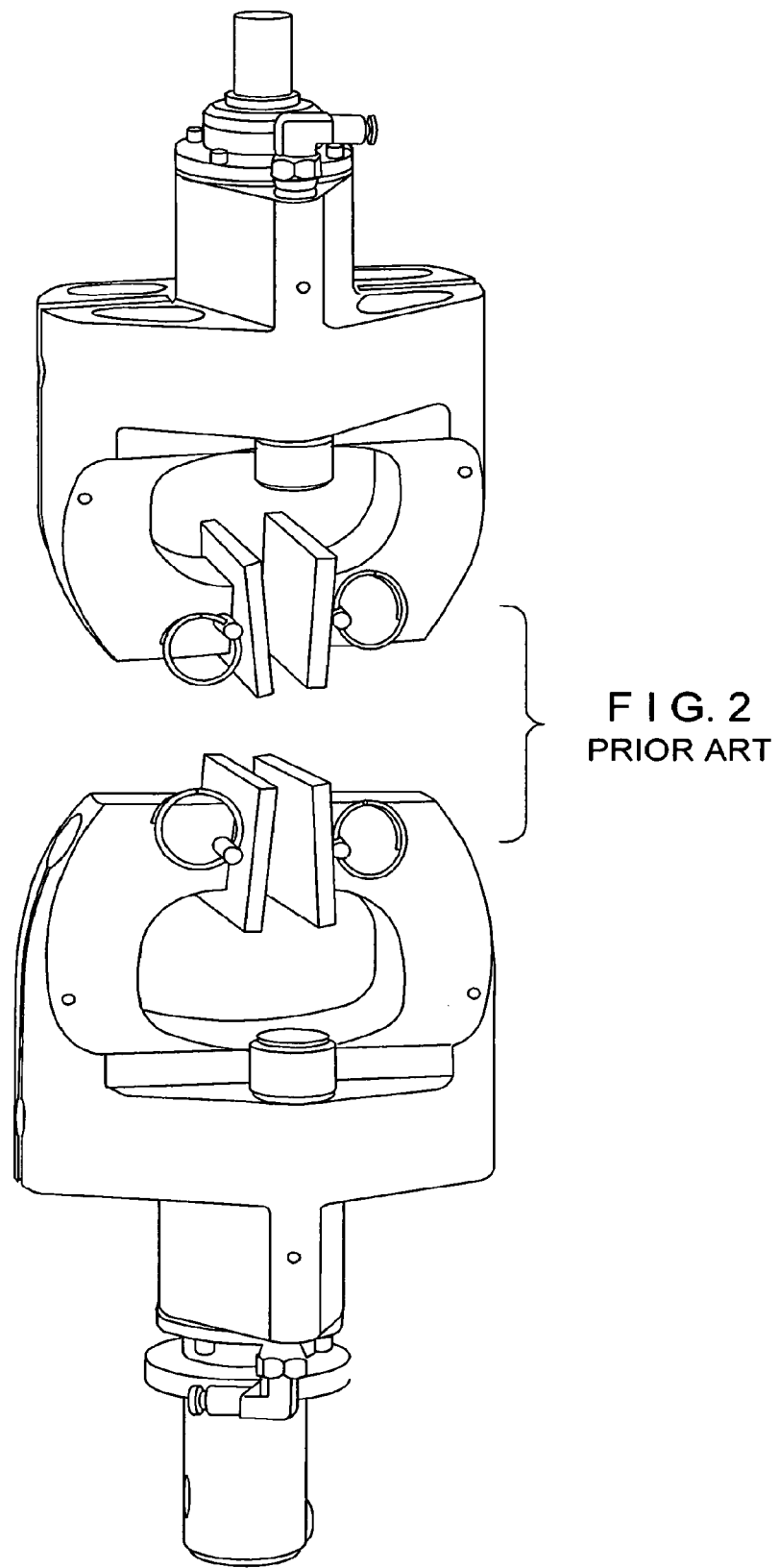
FIG. 2 illustrates typical prior art external pin and aperture connection apparatus.
Figure 3:
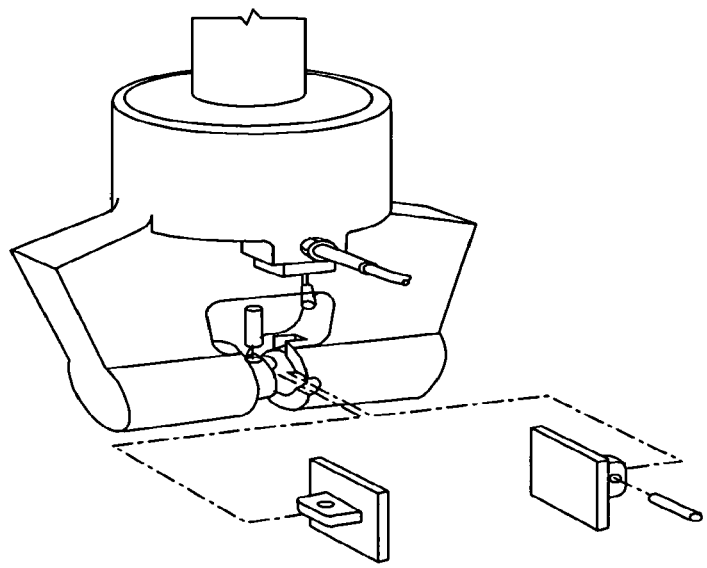
FIG. 3 illustrates typical prior art set screw and groove connection apparatus.
Figure 4:
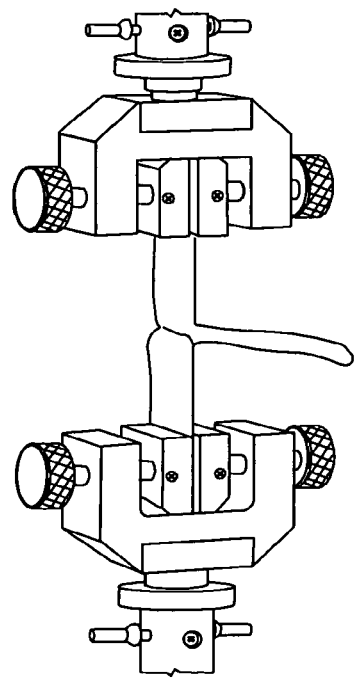
FIG. 4 illustrates typical prior internal pin and aperture connection apparatus.
Figure 5A:
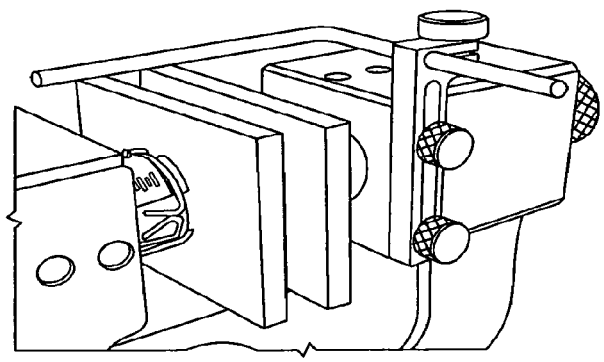
FIGS. 5A and 5B illustrate typical prior art internal pin and retention wire connection apparatus.
Figure 5B:
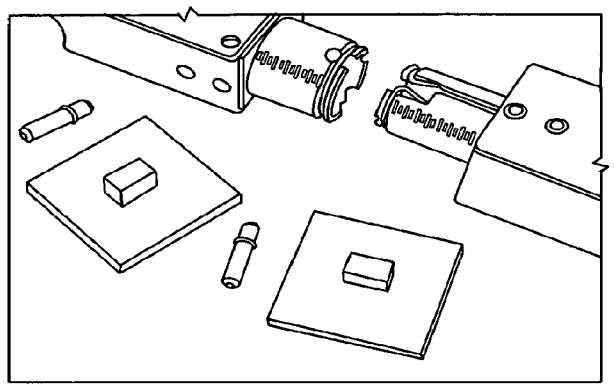
Figure 6:
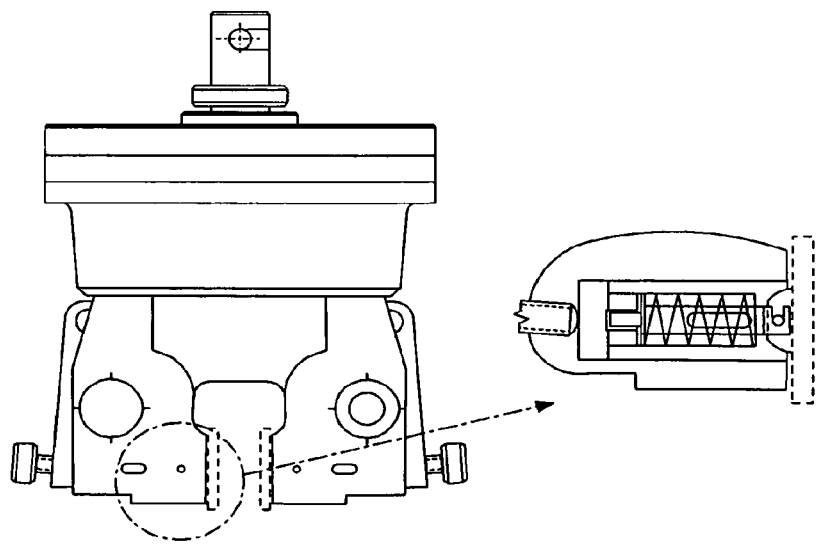
FIG. 6 illustrates typical hook and fixed pin connection apparatus.
Figure 7:
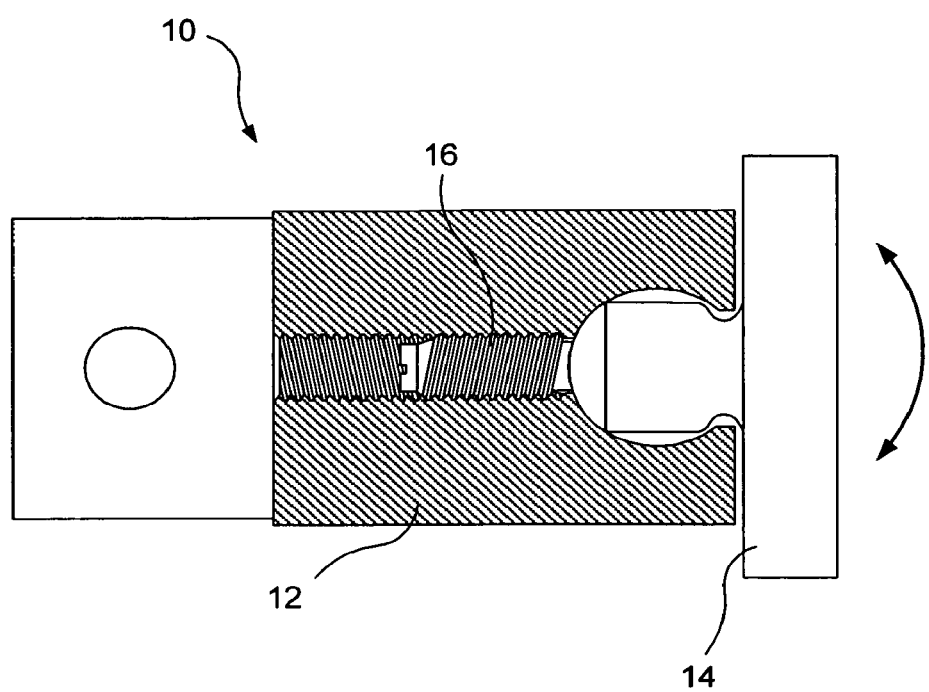
FIG. 7 is a side view of the rotating dovetail connection assembly of an embodiment of the present invention.
Figure 8:
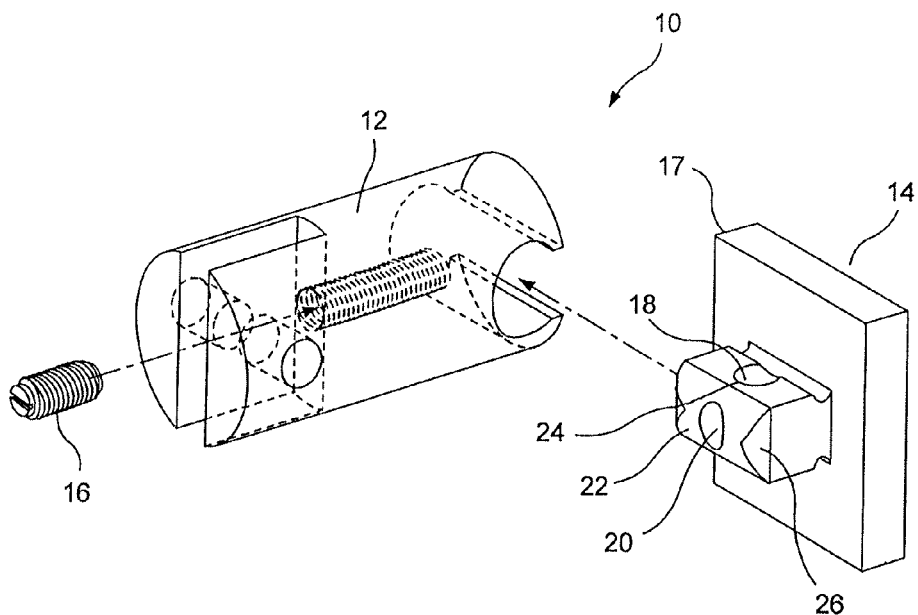
FIG. 8 is an exploded isometric view of the rotating dovetail connection assembly of an embodiment of the present invention.

Referring now to the drawings in detail wherein like numerals refer to like elements throughout the several views, one sees that FIG. 7 shows the rotating dovetail connection 10 which includes cylindrical holder device (or holder) 12, the gripping device 14 (which can be configured as a removable jaw face), and the threaded latching mechanism 16, configured as a spring-loaded ball plunger. Other possible configurations of latching mechanism 16 include a press-in plunger without threading. As shown in FIGS. 7 and 8, the rotating dovetail connection 10 is compromised of these three parts 12, 14, 16. The direction of rotation is also shown in FIG. 7.

As shown in FIG. 8, the gripping device 14 includes plate 17 and tongue 18. Tongue 18 further includes a detent 20 on inner face 22 and a cross aperture 24 passing through tongue 18 parallel to plate 17. Cross aperture 24 is oriented vertically in FIG. 8. The detent 20 is engaged by latching mechanism 16 which is configured as a spring loaded ball plunger. The spring loaded ball plunger 16 both accurately locates and secures the gripping device 14 relatively to the cylindrical holder device 12. The cross aperture 24 in the gripping device 14 serves as a connection point for a traditional pin and aperture connection, allowing for the gripping device 14 to be used on accessories with this connection style. The gripping device 14 also utilizes a sloped surface 26 on an end (or ends) of tongue 18 on to better facilitate insertion of the gripping device 14 into the holding device 12.

Figure 9:
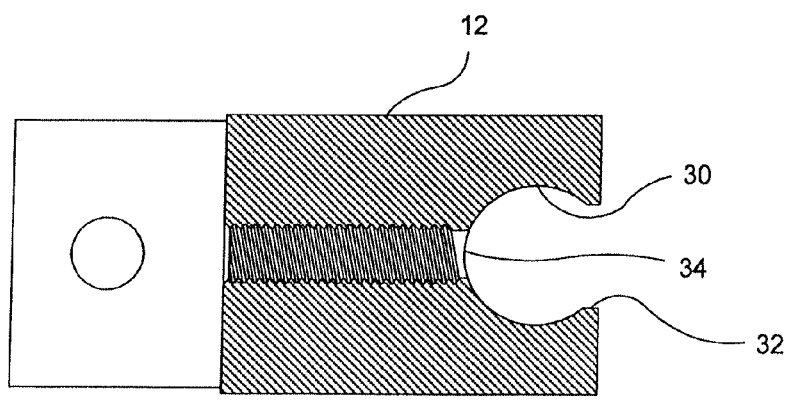
FIG. 9 is a cross-sectional view of a holder of an embodiment of the present invention.

The cross-sectional view of the holding device 12 in FIG. 9 illustrates the details needed for the female end of the rotating dovetail connection 10. A transverse circular bore 30 is formed in the cylindrical holder device 12. A cross cut 32 is formed to create a space for the gripping device 14 to slide into the cylindrical holder device 12. A central longitudinal aperture 34 is formed to accept the latching mechanism 16. Holding device 12 can be engaged by a materials testing accessory, such as a pneumatic, hydraulic or screw-action grip.

The profile of the gripping device 14, which exhibits the male end of the rotating dovetail connection 10, is shown in FIG. 10. The inner face 22 includes a rounded portion 40 on the end of the tongue 18 with a radius corresponding to that of the bore radius of transverse circular bore 30 of the is similar in radius to the matching bore radius on the cylindrical holder device 12. Tongue 18 further includes undercut 42 immediately adjacent to plate 17. Undercut feature 42 serves to secure the gripping device 14 within the cylindrical holder device 12 from moving laterally in the negative Z direction as shown on FIG. 10. Additionally, the lateral flat portions 44 on the tongue 18 allow the gripping device 14 to be used on prior art pin and aperture equipment.

When the rotating dovetail connection 10 is not put under any extraneous load, the ball plunger 16 forces the gripping device 14 in the negative Z direction against the transverse circular bore 30 of the holder device 12. When an extraneous load is applied to the gripping device 14 in the positive Z direction, the ball plunger 16 is compressed, the rounded surface 22 mates up with the transverse circular bore 30, and the connection is free to rotate about the X-axis axis in FIG. 10 (Y-axis in FIG. 9).

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. A jaw face for materials testing comprising:
   a plate with a first planar surface and a second planar surface;
   a tongue extending from the first planar surface, the tongue including:
      a longitudinal axis parallel to the first planar surface;
      a first end, a second end, a first side and a second side which are perpendicular to the first planar surface; and
      a face with edges contacting distal edges of the first end, second end, first side and second side;
   the face having a convex partially cylindrical shape and including a detent depression, and further including first and second chamfered portions extending to the distal edges of the first end and second end;
   an aperture extending through the tongue perpendicular to the longitudinal axis with a first opening on the first side and a second opening on the second side;
   a first undercut section at an intersection of a proximal edge of the first side of the tongue and the first planar surface; and
   a second undercut section at an intersection of a proximal edge of the second side of the tongue and the first planar surface.

2. The jaw face of claim 1 wherein the first side and the second side of the tongue are parallel to the longitudinal axis of the tongue.

3. The jaw face of claim 1 wherein the first end and the second end of the tongue are perpendicular to the longitudinal axis of the tongue.

4. The jaw face of claim 1 wherein the second planar surface is a gripping planar surface.

* * * * *